United States Patent [19]

Nycz

[11] Patent Number: 5,279,935
[45] Date of Patent: Jan. 18, 1994

[54] METHOD OF IMMUNOSSAY INCLUDING DEACTIVATION OF ENDOGENOUS ALKALINE PHOSPHATASE

[75] Inventor: Colleen M. Nycz, Raleigh, N.C.

[73] Assignee: Becton, Dickinson and Company, Franklin Lakes, N.J.

[21] Appl. No.: 486,650

[22] Filed: Mar. 1, 1990

[51] Int. Cl.$^5$ .................. C12Q 1/00; C12Q 1/42; G01N 33/53; G01N 33/566; G01N 33/543

[52] U.S. Cl. .................. 435/5; 435/7.9; 435/7.92; 435/7.93; 435/7.94; 435/7.95; 435/21; 436/501; 436/518

[58] Field of Search .................. 435/5, 7.9, 7.92, 7.93, 435/7.94, 7.95, 21; 436/501, 578

[56] References Cited

U.S. PATENT DOCUMENTS

| | | | |
|---|---|---|---|
| 3,888,629 | 6/1975 | Bagshawe | 23/230 B |
| 4,246,339 | 1/1981 | Cole et al. | 435/7 |
| 4,277,560 | 7/1981 | Gray et al. | 435/7 |
| 4,632,901 | 12/1986 | Valkirs et al. | 435/5 |
| 4,656,128 | 4/1987 | Chlebowski et al. | 435/7 |
| 4,738,932 | 4/1988 | Yabusaki | 436/511 |
| 4,782,016 | 11/1988 | Norton | 435/21 |
| 4,812,293 | 3/1989 | McLaurin et al. | 422/69 |
| 4,946,776 | 8/1990 | Ritterband | 435/21 |
| 4,956,302 | 9/1990 | Gordon et al. | 436/161 |

OTHER PUBLICATIONS

The Merck Index 10th (1983) pp. 330–331.
The Merck Index 10th Ed. (1983) Entry 3489.
Schlesinger, J. Biol. Chem. 1965 240:4284 The reversible dissociation of . . .
McComb et al., Alkaline Phosphatase, Plenum Publ., New York, New York, 1979, p. 413.
Holt et al., Proceedings of the Royal Society of London, B, 1958, 148, 481–494.

*Primary Examiner*—Christine M. Nucker
*Assistant Examiner*—David R. Preston
*Attorney, Agent, or Firm*—Donna R. Fugit

[57] ABSTRACT

A method for immunoassay for a ligand is performed on a porous membrane with alkaline phosphatase as the label. The assay protocol includes a wash step with an organic acid to deactivate endogenous alkaline phosphatase. The invention includes a kit of materials for performing the assay.

17 Claims, 1 Drawing Sheet

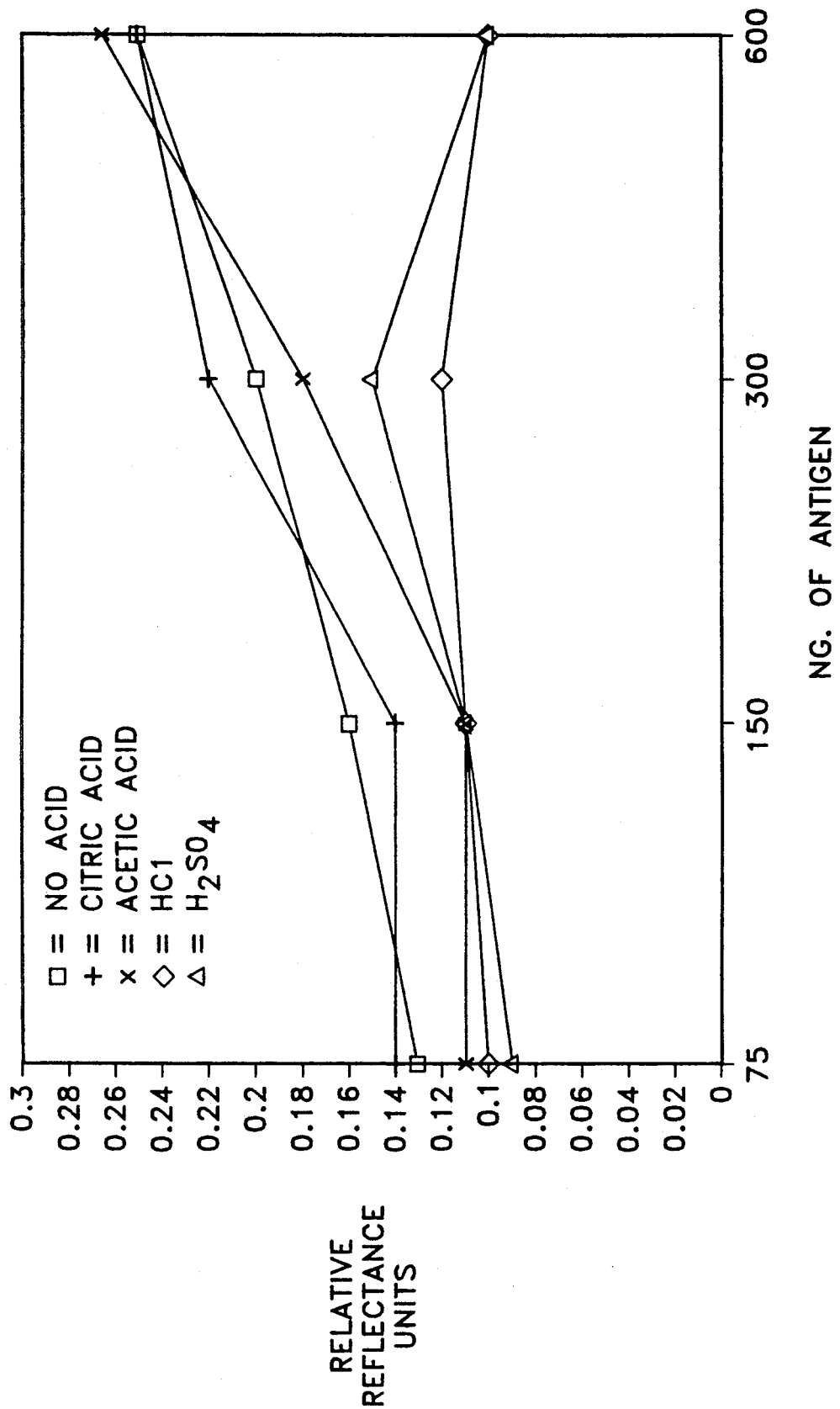

5,279,935

METHOD OF IMMUNOSSAY INCLUDING DEACTIVATION OF ENDOGENOUS ALKALINE PHOSPHATASE

BACKGROUND OF THE INVENTION

1. Field of the Invention

This invention relates to immunoassay for an analyte, and more particularly relates to membrane immunoassay and particular reagents useful therein.

2. Background Information

Assay systems which are both rapid and sensitive have been developed to determine the concentration of a substance, generally referred to as the analyte, present in low concentration in a fluid sample. Immunoassays depend on the binding of an antigen or hapten to a specific antibody and have been particularly useful because they give high levels of specificity and sensitivity. These assays employ one of the above reagents in labeled form, the labeled reagent being referred to as the tracer.

Enzymes have often been used as labels in immunoassay. In conventional enzyme immunoassay (EIA), the enzyme is covalently conjugated with one component of a specifically binding antigen-antibody pair, and the resulting enzyme conjugate is reacted with a substrate to produce a signal which is detected and measured. The signal may be a color change, detected with the naked eye or by a spectrophotometric technique, or may be conversion of the substrate to a product detected by fluorescence.

A convenient format for EIA is solid phase immunoassay in which one of the assay reagents is immobilized on a solid support. The solid support may be in the form of a dipstick, the inside wall of a test tube or cuvette or the well of a microtiter plate. A particularly useful solid support is a microporous membrane.

Membrane immunoassay is often referred to as flow-through assay. Examples of flow-through EIA wherein flow is generated by capillary action are the Bagshaw, U.S. Pat. No. 4,246,339 to Cole et al. and U.S. Pat. No. 4,632,901 to Valkirs et al. U.S. Pat. No. 4,277,560 to Gray and U.S. Pat. No. 4,812,293 to McLaurin et al. are examples of flow-through assays using pressure and vacuum respectively.

In membrane EIA, any number of liquids may be caused to flow-through the membrane to effect binding, separation and washing of assay components. The final step in most membrane EIA procedures is passage of a color developing reagent, such as a chromogen, through the membrane. The chromogen reacts with enzyme captured on the membrane to produce a color change which may be detected as evidence of the presence of analyte or measured as evidence of the concentration of analyte.

An enzyme commonly used in immunosassay is alkaline phosphatase (AP). This enzyme is present in practically all cells, and has as its principle function the removal of phosphate groups. It has been extensively studied, and is well-known to be deactivated at low pH (Schlesinger et al., *Journal of Biological Chemistry*, 240, 4284 (1965); McComb et al., *Alkaline Phosphatase*, Plenum Publ., New York, N.Y., 1979, p 413).

A problem often encountered in colorimetric assays using AP as the label results from the ubiquitous nature of the enzyme. Most assays for an antigen in a clinical sample are performed without isolation of the antigen. If AP is present in the sample (hereinafter referred to as endogenous AP), it may undergo nonspecific binding to the membrane or one of the assay components, or may not be completely removed by wash steps in the assay protocol. In such a case, positive signals from clinically negative samples may result. The present invention is directed to overcoming this problem.

SUMMARY OF THE INVENTION

A flow-through assay method for determining a ligand suspected to be present in a liquid clinical sample includes passing the sample through a membrane coated with an inert protein whereby the ligand attaches to the membrane. In another embodiment of the method, the membrane additionally has coated thereon an antiligand which binds specifically to the ligand. In the present disclosure, the term inert protein means a protein which is immunologically unreactive toward any other component of the assay and which does not substantially bind nonspecifically to other proteins in the assay medium, with the understanding that the inert protein may well be immunologically reactive toward other materials which are not part of the assay of the invention.

After the sample has passed through the membrane to effect binding, a solution of an organic acid is passed through the membrane to deactivate endogenous AP in the sample. A tracer which includes AP is then incubated with antigen on the membrane to cause binding of the tracer to the antigen. The AP bound to the membrane is contacted with a substrate comprising an indoxyl derivative which is converted to a colored insoluble product which precipitates as a visible spot on the membrane. Preferred substrates additionally include a tetrazolium salt. The contrast between the color of the spot and the background color may if desired be stabilized for later viewing by passing a color stopping and stabilizing solution through the membrane.

Preferred ligands are viral antigens detected by an assay format in which the AP component of the tracer is conjugated to a specific antibody. Preferred deactivating acids are hydroxy polycarboxylic acids, the most preferred of which is citric acid.

The invention includes a kit of materials useful in performing the assay of the invention.

Thus the invention provides a flow-through assay for an antigen in a clinical sample using AP as the label and an organic acid wash to deactivate endogenous AP in the sample. While deactivation of AP at low pH is a well-known phenonmenon, the organic acid wash of the invention selectively deactivates endogenous AP without denaturing the antigen itself. In contrast, deactivation of endogenous AP with mineral acid would prevent binding between antigen and tracer and would destroy the assay.

BRIEF DESCRIPTION OF THE DRAWING

The FIGURE shows the results of an assay for Influenza virus in accordance with the assay of the invention.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

One aspect of the present invention is a method for colorimetric flow-through immunoassay of a ligand in a liquid using AP as the label. In accordance with the invention, it has been discovered that endogenous AP, often present in clinical samples, may be deactivated by washing the membrane with an organic acid, preferably a hydroxy polybasic acid, so that the color which develops on the membrane is due to ligand only.

The assay of the invention may be performed in any suitable assay device adapted for flow-through assay as known in the art. In preferred devices, flow of assay liquids is promoted by capillary action induced by a pad of absorbent material positioned below the membrane. Many such devices have been disclosed and several are commercially available. The device itself does not represent a feature of the invention.

The ligand may be from any source, and may be an antigen, an antibody or a hapten. For example, the ligand may be an antigen present in a body fluid, or it may be isolated from a body fluid and subsequently introduced into a different liquid, such as buffer. In other cases, the ligand may be from a source other than a body fluid, as, for example, a culture of microorganisms such as Chlamydia or a cellular extract thereof. Preferred ligands are antigens, most preferably viral antigens present in a body fluid, such as Adenovirus, Parainfluenza 3 virus and, most preferably, Herpes simplex virus (HSV), Respiratory syncytial virus (RSV), and Influenza A (Flu A). The invention will hereinafter be described generically in terms of a viral antigen.

Turning now to a detailed description of the assay components, the porous membrane may be of any material which does not interfere in any way with any other component or step of the assay. Suitable membranes are, for example, glass fiber, polyvinylidene difluoride, polycarbonate, nitrocellulose and nylon. Such membranes are well-known in the art and many are commercially available from suppliers such as Pall, Glen Cove, N.Y.; Millipore, Bedford, Mass.; and Schleicher and Schuell, Keene, N.H.

The membrane may be coated with an antiligand specific for the ligand. Thus, in the case where the ligand is the preferred viral antigen, the antiligand may be an antibody which binds specifically to the antigen and thereby captures the antigen on the membrane. The membrane may be further coated with an inert protein to fill any binding sites on the membrane not occupied by the capture antibody. Representative nonlimiting examples of suitable inert proteins are casein and albumin, although others will be evident to those skilled in the art. Coating of both the inert protein and the antibody to the membrane may be carried out by any suitable method, preferably by incubating the membrane with a solution of the protein whereby the protein is physically absorbed into the polymeric matrix of the surface of the membrane.

In a preferred embodiment of the invention, the membrane is coated with the inert protein, the antigen absorbed directly onto this surface and the assay performed without a capture antibody. Flow-through immunoassay without a capture antibody is disclosed in copending application Ser. No. 272,380, filed Nov. 17, 1988, of common assignee herewith.

The membrane having a coating of capture antibody and/or inert protein is exposed to the sample suspected of containing the viral antigen. Preferably, the coated membrane is incubated with the sample in a transient, flow-through format for about 1 to 15, preferably about 5 minutes at a temperature of about 0° to 50° C., preferably about ambient temperature. By this procedure, antigen in the sample is captured on the coated membrane in proportion to its concentration in the sample. In addition, it has been found that viral antigen is absorbed preferentially even when the sample contains a large excess of extraneous protein, such as is the case when the sample is a body fluid.

Subsequent to the incubation, a wash solution containing a reagent to deactivate any endogenous AP is passed through the membrane. Any organic acid which deactivates endogenous AP without affecting any other aspect of the assay may be used. Monobasic acids such as lactic or acetic acids may be used. Preferred acids are polybasic acids such as succinic and glutaric acids. The most preferred acids are hydroxy polybasic acids such as malic and tartaric acid, and, in particular, citric acid. The deactivating acid may preferably be passed through the membrane as a solution in water, buffer or saline. Preferably an aqueous solution of about 0.05 to 1.0M, preferably about 0.1 to 0.2M having a pH of about 1-3 may be used. For most clinical samples, about 300 μL of the solution is sufficient to deactivate whatever endogenous AP is present. For samples suspected to have high concentrations of endogenous AP, more acid solution may be used.

The tracer comprises AP conjugated to either the antigen (competitive assay) or a detection antibody (sandwich assay) as described below. Many preparations of AP from various sources are commercially available and may serve as the label as long as they may be conjugated to the antigen or antibody. Conjugation of AP to antigens or antibodies is well-known and fully understood by those skilled in the art.

Any substrate for AP as known in the art may be used. Preferred substrates are those which form an insoluble precipitate on the membrane. The most preferred substrates are indoxyl derivatives, such as indoxyl phosphate. Other indoxyl substrates as known in the art may be used, as for example, 5-bromo-4-chloroindoxyl derivatives. An extensive list of indoxyls useful for preparation of suitable indoxyl derivatives by standard methods is given by Holt et al., *Proceedings of the Royal Society of London, B*, 1958, 148, 481–494. The substrate may preferably be dissolved in water, saline or a suitable buffer.

It is preferred that the color resulting from the cleavage of the indoxyl substrate be augmented by inclusion of a tetrazolium salt in a substrate composition. Suitable tetrazolium salts are, for example, p-iodonitrotetrazolium violet (INT) and nitroblue tetrazolium (NBT). Although a colored spot of sufficient intensity for visualization develops in the absence of the tetrazolium salt, inclusion of this reagent gives a spot of deeper color which may be more easily visualized and may accordingly increase the sensitivity of the assay.

The membrane assay of the invention may be performed by either the competitive or sandwich technique wherein liquid flow-through the membrane may be by capillary action induced by absorbent material positioned under the membrane. In the competitive assay of the invention, the tracer is the antigen having AP conjugated thereto wherein the antigen and the tracer compete for available binding sites on the coated membrane. In the preferred sandwich assay format of the invention, the tracer is a detection antibody specific for the antigen conjugated to AP. The preferred detection antibody is a monoclonal antibody raised by conventional procedures well-known in the art. The substrate composition may then be passed through the membrane. AP on the membrane converts the substrate to a product detectable by color. The extent of color formation is proportional to antigen concentration, which may be determined by assaying liquid samples having predetermined quantities of antigen therein and comparing color intensities.

If desired, the color forming reaction may be stopped and the color on the membrane substantially stabilized by passing a solution of a color stabilizing reagent through the membrane. Suitable stabilizing reagents are mineral acids such as hydrochloric, sulfuric, phosphoric and pyrophosphoric acids or an aqueous solution of an organic acid, optionally containing an organic solvent. Suitable organic acids are, for example, acetic, tartaric, oxalic succinic, benzoic and preferably citric acids. Suitable organic solvents are methanol, ethanol, isopropanol, acetone and tetrahydrofuran. The concentration of the stabilizing acid may be about 0.1 to 0.5, molar in water or buffer which may optionally contain about 30 to 70% by weight of the organic solvent. Further details with respect to the color stabilizer are given in copending application Ser. No. 414,161, filed Sep. 28, 1989, of common assignee herewith.

Another aspect of the invention is a reagent kit or package of materials for performing an assay for a ligand in accordance with the method of the invention. The kit may include a membrane coated with an inert protein and optionally with a capture antiligand, a tracer comprising AP conjugated to one of the ligand or a detection antiligand, a substrate for AP and a solution of an organic acid, preferably a dibasic acid, to deactivate endogenous AP. The kit may also include a color stabilizer comprising a solution of an acid, preferably an aqueous solution which includes an organic solvent. The kit may also include standards for the ligand, as, for example, one or more ligand samples of known concentration, or it may include other reagents, substrates, or solutions, such as saline or buffers and utensils such as vials or droppers useful in carrying out the assay. The membrane may be provided in a housing, preferably plastic, containing a material positioned under the membrane, such as absorbent paper, to facilitate flow of assay liquids through the membranes by capillary action.

The following examples are provided to further describe the invention but are not to be considered in any way as limitative of the invention.

EXAMPLE I

Assay for Influenza A Virus

A membrane filter stack was assembled with the following configuration:

Top layer—Three micron Biodyne ® Membrane, (Pall, Glen Cove, N.Y., #BIA0030HC5). Precoated by immersion in phosphate buffered saline containing 0.3% casein for 30 minutes at ambient temperature.

Next layer—Non-woven rayon sheet (Schleicher and Schuell, Keene, N.H.; #5-S).

Bottom layer—Cellulose absorbent pads (2) (Filtration Sciences, Mount Holly Springs, Pa.; #ED 320-200)

The membrane layers were encased in a plastic holder which includes a receiving well formed above the top layer. Within this well was fitted a flow restriction insert which has an aperture more narrow than the receiving well and sits flush against the top membrane.

An antigen stock was prepared with type A influenza virus (Flu-A) (WSN strain) infected Madin-Darby canine kidney (MDCK) cells diluted in a buffer containing: 250 mM Tris HCl, 10 mM ethylenediaminetetraacetic acid (EDTA), 1 mM ethylenebis(oxyethylenenitrilo)tetraacetate (EGTA), 4% (v/v) polyoxyethylene sorbitan monolaurate (Tween 20), 1% N-acetyl-L-cysteine, 0.2% sodium azide ($NaN_3$), pH 8.5. Control antigen was prepared in a similar manner from uninfected MDCK cells.

A 250 µL aliquot of this antigen (or control) was applied to the device and allowed to drain through the flow restriction insert and onto the top membrane layer, followed by passage of 300 µL of an aqueous solution of 0.15M citric acid. The flow restriction insert was then removed, and to the device was added 150 µL of tris buffered saline (TBS), additionally containing 1 mg/mL of rabbit IgG.

A solution containing 27 µg/mL of anti-Flu-A antibody conjugated to alkaline phosphatase calf intestine AP, Buehringer Mannheim, Indianapolis, Ind. was prepared in a buffer containing 100 mM Tris HCl, 150 mM NaCl, 200 mM sodium phosphate, 1% casein, 1 mM magnesium chloride, 0.1 mM zinc chloride, 1 mM 2-mercaptoethanol, and 0.2% $NaN_3$, pH 7.2. A 150 µL aliquot of this mixture was added to the device and allowed to absorb into the membrane stack. Following a brief (two minute) incubation, the device was washed with 300 µL of TBS (without IgG).

A 150 µL solution containing 0.33 mg/mL nitroblue tetrazolium, 1% methanol, and 0.2% $NaN_3$ was added to the device. This was followed by the addition of 150 µL of a solution containing 2 mg/mL indoxyl phosphate, 16 mM levamisole in 50 mM 2-amino-2-methyl-1-propanol (AMP) acetate, 0.2% $NaN_3$, 1 mM magnesium chloride, at pH 9.8. Following a five minute incubation at ambient temperature, the color forming reaction was stopped by the addition of 150 µL of a stabilizing solution containing 150 mM sodium citrate at pH 3.0. The relative color density of the resulting signal spots was measured in arbitrary units of reflectance with a reflectance densitometer (Gretag, Seattle, Wash., model 183). The results of an experiment performed with a series of antigen dilutions are presented in the FIGURE and are compared with a negative control (no acid) and with results obtained using 1N HCl, 4.5N $H_2SO_4$, 5% acetic acid. It is readily seen that reflectance increased with increasing antigen concentration when acetic and citric washes (and no acid) were used, indicating successful assay. However, HCl and $H_2SO_4$ gave unsuccessful assays in that reflectance did not increase with increasing antigen concentration. While not wishing to be bound by any theory, it is believed that mineral acid denatured the antigen on the membrane and prevented binding to conjugate antibody.

EXAMPLE II

Comparison of Deactivating Acids

I. Using the membrane filter stack, plastic holder and assay protocol as described in Example I, the deactivating acids listed below were compared for effectiveness in deactivating endogenous AP in infected and uninfected MDCK cells.

A . . . 0.15M citric acid
B . . . 0.15M glutaric acid

C ... 0.15M tartaric acid
D ... 0.15M succinic acid
E ... 0.15M malic acid
F ... 0.15M lactic acid
G ... no acid - negative control The results of this experiment are given in the following Table.

| ng of cells | Reflectance (arbitrary units) acid | | | | | | |
|---|---|---|---|---|---|---|---|
| | A | B | C | D | E | F | G |
| 600[a] | .23(+)[c] | .21(+) | .22(+) | .25(+) | .24(+) | .28(+) | .25(+) |
| 300[a] | .21(+) | .17(+) | .18(+) | .18(+) | .18(+) | .19(+) | .20(+) |
| 150[a] | .14(+) | .14(+) | .14(+) | .15(+) | .16(+) | .15(+) | .16(+) |
| 75[a] | .12(+) | .13(+) | .13(+) | .15(+) | .14(+) | .12(+) | .13(+) |
| 600(−)[b] | .12(−) | .10(−) | .10(−) | .10(−) | .12(−) | .12(−) | .10(−) |

[a]WSN infected MDCK cells
[b]uninfected MDCK cells
[c](+) and (−) indicate presence or absence of visually detected color It is seen from the above Table that the presence of the organic acid did not interfere with the assay of infected cells and that the experiment performed with uninfected cells (no antigen) gave negative signals with each acid indicating deactivation of endogenous AP in these cells.

II. Example I was repeated except no MDCK cells were used, and the dilution buffer was spiked with 4.8 units/test of $E.\ coli$ AP. Thus, in this experiment, no antigen was present so that no label AP was captured on the membrane and the $E.\ coli$ AP spike, representing endogenous AP, was the only AP present. The results of this experiment are as follows.

| acid | reflectance | visual |
|---|---|---|
| A | .03 | (−) |
| B | .06 | (+) |
| C | .04 | (−) |
| D | .06 | (+) |
| E | .06 | (+) |
| F | .06 | (+) |
| G | .09 | (+) |

It is seen from this experiment that all of the deactivating acids (A to F) reduced the signal due to the AP spike in comparison to the control (G) having no acid, and that citric acid (A) and tartaric acid (C) were the most effective.

What is claimed is:

1. A method for determining a ligand in a liquid sample comprising:
   a) causing a liquid sample suspected of containing a ligand to pass through a porous membrane coated with an inert protein whereby said ligand becomes affixed on the coated membrane;
   b) passing a wash solution containing an organic polybasic acid through said membrane;
   c) passing a solution containing a tracer comprising alkaline phosphatase conjugated to an antiligand through said membrane whereby said tracer binds to said ligand;
   d) passing a substrate solution for said alkaline phosphatase comprising a tetrazolium salt and an indoxyl derivative through said membrane, said substrate being converted by said alkaline phosphatase on said membrane to a colored product; and
   e) determining the presence of said ligand in said first liquid by detecting said colored product on said membrane.

2. The method of claim 1 wherein said ligand is selected from the group consisting of an antigen, an antibody and a hapten.

3. The method of claim 2 wherein said antigen is a viral antigen.

4. The method of claim 3 wherein said viral antigen is selected from the group consisting of Herpes simplex virus, Respiratory syncytial virus and Influenza A virus.

5. The method of claim 1 wherein said inert protein is selected from the group consisting of casein and albumin.

6. The method of claim 1 wherein said polybasic acid is selected from the group consisting of citric, succinic, glutaric, malic and tartaric acids.

7. The method of claim 1 further comprising directing a color stabilizing solution through said membrane.

8. A method for determining a ligand in a liquid comprising:
   a) causing a liquid sample suspected of containing a ligand to pass through a porous membrane coated with a reagent selected from the group consisting of an antiligand and an inert protein whereby said ligand becomes affixed on said coated membrane;
   b) passing a wash solution containing an organic acid through said membrane;
   c) passing a solution containing a tracer comprising alkaline phosphatase through said membrane whereby said tracer attaches to one of said antiligand and said ligand to give a bound fraction including said alkaline phosphatase on said membrane;
   d) passing a substrate solution for said alkaline phosphatase comprising an indoxyl derivative through said membrane to give a colored product; and
   e) determining the presence of said ligand in said first liquid by detecting said colored product on said membrane.

9. The method of claim 8 wherein said acid is selected from the group consisting of a monobasic acid and a polybasic acid.

10. A method for determining a viral antigen in a liquid sample comprising:
    a) causing a liquid sample suspected of containing a viral antigen to pass through a membrane coated with an inert protein whereby said viral antigen becomes affixed on said coated membrane;
    b) passing a wash solution containing citric acid through said membrane;
    c) passing a solution containing an antibody conjugated to alkaline phosphatase through said membrane whereby said antibody binds to said antigen to give a bound fraction including said alkaline phosphatase on said membrane;

d) passing a substrate solution containing indoxyl phosphate and nitroblue tetrazolium through said membrane, said alkaline phosphatase converting said indoxyl phosphate and nitroblue tetrazolium to a colored product on said membrane;

e) directing a color stabilizing solution comprising citric acid through said membrane; and f) determining the presence of said antigen in said first liquid by detecting said colored product on said membrane.

11. A kit of materials for performing an assay for a ligand in a liquid comprising a membrane coated with at least one of an inert protein and a first antiligand, a tracer comprising alkaline phosphatase conjugated to one of said ligand and a second antiligand, a substrate for said alkaline phosphatase and a wash solution comprising an organic dibasic acid.

12. The kit of claim 11 wherein said inert protein is selected from the group consisting of albumin and casein.

13. The kit of claim 11 wherein said substrate comprises an indoxyl phosphate.

14. The kit of claim 13 wherein said substrate further comprises a tetrazolium salt.

15. The kit of claim 11 wherein said acid is selected from the group consisting of citric and tartaric acids.

16. The kit of claim 11 further comprising at least one solution selected from the group consisting of a solution devoid of ligand and a solution containing a known concentration of ligand.

17. The kit of claim 11 further comprising a housing having said membrane therein and an absorbent material positioned adjacent said membrane.

* * * * *